United States Patent [19]
Suzuki et al.

[11] Patent Number: 6,127,409
[45] Date of Patent: Oct. 3, 2000

[54] ASCORBIC ACID DERIVATIVE AND VITAMIN C PREPARATION CONTAINING THE SAME

[75] Inventors: Masahiro Suzuki; Toshi Tsuzuki, both of Chiba; Shinobu Ito; Eiji Ogata, both of Tokyo, all of Japan

[73] Assignee: Showa Denko Kabushiki Kaisha, Tokyo, Japan

[21] Appl. No.: 09/070,012

[22] Filed: Apr. 30, 1998

Related U.S. Application Data

[60] Provisional application No. 60/075,585, Feb. 23, 1998.

[30] Foreign Application Priority Data

Apr. 30, 1997  [JP]  Japan ..................... 9-113092

[51] Int. Cl.$^7$ .................... A01N 43/08; C07D 307/02
[52] U.S. Cl. ............................. 514/473; 549/477
[58] Field of Search ............... 549/477; 514/473

[56] References Cited

FOREIGN PATENT DOCUMENTS

| A20339486 | 11/1989 | European Pat. Off. . |
| A30339486 | 11/1989 | European Pat. Off. . |
| A20436936 | 7/1991 | European Pat. Off. . |

*Primary Examiner*—John Kight
*Assistant Examiner*—Raymond Covington

*Attorney, Agent, or Firm*—Sughrue, Mion, Zinn, Macpeak & Seas, PLLC

[57] ABSTRACT

A novel ascorbic acid derivative having both sufficiently improved stability and liposolubility, and facilitated cellular uptake. Also disclosed is a process for producing the derivative and a composition capable of effectively providing the action of vitamin C, for use in medical preparations, agricultural chemicals, animal drugs, foods, feeds or cosmetic preparations. The ascorbic acid derivative is a compound represented by the following formula (1) or a salt thereof:

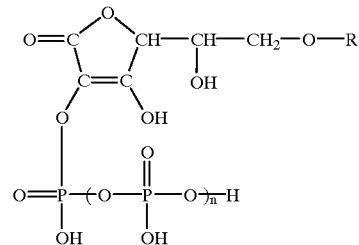

(1)

wherein R represents an acyl group having eleven or more carbon atoms and n is 0, 1 or 2.

7 Claims, No Drawings

ASCORBIC ACID DERIVATIVE AND VITAMIN C PREPARATION CONTAINING THE SAME

CROSS REFERENCE TO RELATED APPLICATIONS

This application is an application filed under 35 U.S.C. §111 (a) claiming benefit pursuant to 35 U.S.C. §119(e) (1) of the filing date of the Provisional Application 60/075,585 filed Feb. 23, 1998 pursuant to 35 U.S.C. §111(b).

FIELD OF THE INVENTION

The present invention relates to a novel ascorbic acid derivative, a vitamin C preparation containing the same and a composition containing the same, such as a cosmetic preparation. The present invention also relates to a novel process for producing the ascorbic acid derivative.

BACKGROUND OF THE INVENTION

The effects of ascorbic acid include the inhibition of lipid peroxidation, acceleration of collagen formation, retardation of melanin formation, enhancement of immune functions and the like. For these purposes, ascorbic acid has hitherto been used in the fields of medical preparations, agricultural chemicals, animal drugs, foods, feeds, cosmetic preparations and the like. However, ascorbic acid has poor aging stability and poor liposolubility. Accordingly, the cumulative amount thereof in cells after permeating through the cell membrane is limited, and the physiological actions of vitamin C cannot be achieved to a satisfactory extent.

To cope with this, various derivatives have been proposed, where the hydroxyl group present in the enediol part at the 2- or 3-position, which is easily oxidized, is transformed into a phosphoric acid ester (as described, for example, in JP-B-52-1819 (the term "JP-B" as used herein means an "examined Japanese patent publication") and JP-A-02-279690 (the term "JP-A" as used herein means an "unexamined published Japanese patent application")) so as to improve stability, or is acylated with a fatty acid to thereby improve liposolubility (as described, for example, in JP-A-59-170085).

Of the conventional ascorbic acid derivatives, compounds having satisfactorily improved stability (for example, magnesium L-ascorbic acid 2-phosphate) still lack adequate liposolubility.

JP-A-58-222078 proposes a 6-O-alkanoyl-ascorbic acid-2- or -3-phosphoric acid ester as a novel compound having increased stability and an appropriate solubility in lipid. The alkanoyl group thereof has less than eleven carbon atoms, and only a pivaloyl group is disclosed as an example thereof. The compound of the present invention cannot be obtained by the production process disclosed in JP-A-58-222078. Furthermore, the novel compound disclosed therein does not have both sufficiently improved stability and liposolubility.

JP-A-61-152613 describes a cosmetic material containing a 6-O-higher acylascorbic acid-2-phosphoric acid ester. In this patent publication: first, transformation into a sulfuric acid ester but not into a phosphoric acid ester is described; second, the ascorbic acid derivative thus obtained is not identified; and third, the results of the working examples thereof are closely similar to those of the working examples of JP-A-61-151107 where the same experiment is performed except for using a 6-O-higher acylascorbic acid-2-sulfuric acid ester. Taking these facts into account, it can be concluded that the ascorbic acid derivative used in JP-A-51-152613 neither discloses nor suggests a 6-O-higher acylascorbic acid-2-phosphate.

EP0339486 and German Patent Publication DE4000397A1 propose compounds such as 6-O-octadecanoyl-2-(O*,O*-diethyl-phosphoryl)-ascorbic acid. However, these compounds are intended to capture active oxygen, and the ethyl group or the like remains bonded to the phosphoric acid group. Therefore, these compounds have deficient stability, are hardly susceptible to the action of phosphatase, and are not easily biotransformed into ascorbic acid.

As described in the foregoing, various L-ascorbic acid derivatives have been proposed, however, an ascorbic acid derivative having sufficiently high stability, appropriate liposolubility, and which is capable of satisfactorily attaining an increased ascorbic acid intracellular cumulative amount has not yet been obtained.

SUMMARY OF THE INVENTION

It is therefore an object of the present invention to provide a novel ascorbic acid derivative having both sufficiently improved stability and liposolubility and facilitated cellular uptake. It is also an object of the present invention to provide an industrial method for easily producing the derivative, and furthermore, a composition capable of effectively bringing out the action of vitamin C, for use in medical preparations, agricultural chemicals, animal drugs, foods, feeds or cosmetic preparations.

Under these circumstances, the present inventors have conducted extensive investigations. As a result, it has been found that the ascorbic acid derivative of the present invention, described below, is a stable compound having an appropriate liposolubility and which is transformed into ascorbic acid with an enzyme in vivo. Also, the compound of the present invention can increase intracellular cumulative amounts because its uptake into cells is facilitated and can effectively provide the physiological action of vitamin C. The present invention has been achieved based on the above findings.

Namely, the above objectives of the present invention have been achieved by providing:

1. An ascorbic acid derivative which is a compound represented by the following formula (1) or a salt thereof:

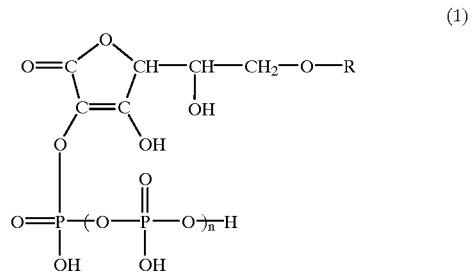

(1)

wherein R represents an acyl group having eleven or more carbon atoms and n is 0, 1 or 2.

2. The ascorbic acid derivative as described in 1 above, wherein n is 0.

3. The ascorbic acid derivative as described in 1 or 2 above, wherein R in formula (1) is selected from the group consisting of a lauroyl group, a myristoyl group, a palmitoyl group and a stearoyl group.

4. The ascorbic acid derivative as described in 1, 2 or 3 above, wherein the salt is a salt of a metal selected from the group consisting of alkali metals, alkaline earth metals, aluminum, iron, zinc and bismuth.

5. A process for producing an ascorbic acid derivative which is a compound represented by formula (1) above or a salt thereof, which comprises reacting an ascorbic acid-2- phosphoric acid ester or 2-pyrophosphoric acid ester or 2-triphosphoric acid ester and/or a salt thereof with at least one of a fatty acid, a fatty acid ester thereof and a salt thereof to produce a compound represented by formula (1) or a salt thereof, wherein R represents an acyl group having eleven or more carbon atoms and n is 0, 1 or 2.

6. A process for producing an ascorbic acid derivative which is a compound represented by the following formula (2) or a salt thereof, which comprises reacting an ascorbic acid-2-phosphoric acid ester and/or a salt thereof with at least one of a fatty acid, a fatty acid ester thereof and a salt thereof to produce a compound represented by the following formula (2) or a salt thereof:

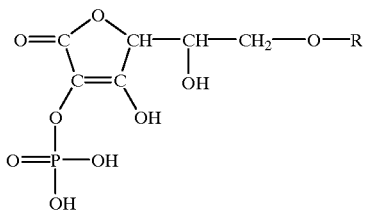

(2)

wherein R represents an acyl group having eleven or more carbon atoms.

7. The process for producing an ascorbic acid derivative as described in 5 or 6 above, wherein said reacting step comprises reacting in the presence of a condensing agent.

8. The process for producing an ascorbic acid derivative as described in 5 or 6 above, wherein said reacting step comprises reacting in concentrated sulfuric acid.

9. A vitamin C preparation containing the ascorbic acid derivative as described in 1 to 4 above as an effective ingredient.

10. A cosmetic preparation, agricultural chemical preparation, animal drug preparation, food or feed composition containing the ascorbic acid derivative as described in 1 to 4 above.

DESCRIPTION OF THE PREFERRED EMBODIMENTS

The present invention is described in detail below.

The ascorbic acid derivative of the present invention is a compound represented by the following formula (1) or a salt thereof:

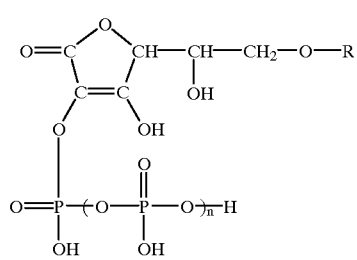

(1)

wherein R represents an acyl group and n is 0, 1 or 2. This compound is stable and difficultly oxidized because the 2-position is esterified. Furthermore, this is a monoester of a higher fatty acid having 11 or more carbon atoms, preferably from 12 to 28 carbon atoms. Therefore, the compound can have appropriate liposolubility and facilitated cellular uptake. Furthermore, because the phosphoric acid group at the 2-position is readily hydrolyzed by phosphatase in vivo, and because the higher fatty acid ester is an ester with a primary alcohol (6-position) susceptible to the action of lipase or esterase, the compound of the present invention is easily biotransformed into ascorbic acid.

The compound represented by formula (1) or a salt thereof of the present invention can be produced according to the following reaction scheme (in the case of n=0 in formula (1)):

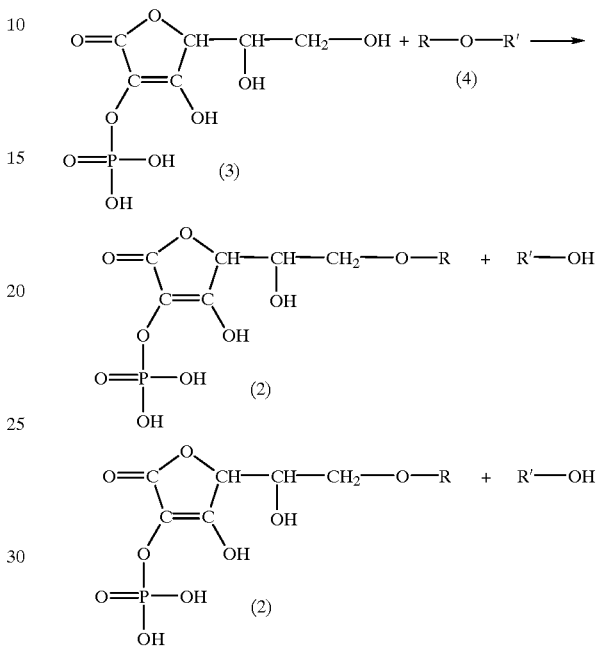

wherein R represents an acyl group having eleven carbon atoms or more and R' represents hydrogen, a cation or an alkyl group.

More specifically, an ascorbic acid-2-phosphate (3) and/or a salt thereof is reacted with (4) which is at least one of a fatty acid, an ester thereof and a salt thereof to produce an ascorbic acid-2-phosphate-6-fatty acid ester (2) or a salt thereof. This reaction is preferably conducted in the presence of a condensing agent. For example, when sulfuric acid is used as the condensing agent, concentrated sulfuric acid, an ascorbic acid-2-phosphate and a fatty acid or an ester or salt thereof are mixed and reacted. The fatty acid ester (wherein in formula (4), R' is analkyl group) is preferably a lower alkyl ester such as a methyl ester or an ethyl ester.

The starting materials may be used in equimolar amounts. However, as long as no problems occur during purification or isolation, one part may be present in slight excess.

The reaction time and the reaction temperature vary depending on whether the fatty acid is a free acid, an ester or a salt, or the kind and the amount of the condensing agent. However, the reaction time is generally from 1 to 120 hours, preferably from 10 to 60 hours, and the reaction temperature is generally from 5 to 70° C., preferably from 15 to 30° C. The amount of water carried over from the starting materials or catalyst into the reaction solution is suitably 10% or less, preferably 2% or less.

Where a solvent is used in this reaction, the sulfuric acid as the condensing agent may be used concurrently as the solvent, or the solvent may be selected from other solvents which can dissolve the starting materials.

The purification or isolation may be performed using a known method such as solvent extraction, washing, salting out or column chromatography. For example, the ester or salt thus obtained may be isolated or purified by ether extraction or hexane washing. If desired, the ester or salt thus obtained may further be isolated or purified by reverse phase chromatography or the like.

The salt of the compound represented by formula (2) can be obtained as a salt with the corresponding base by neutralizing the ascorbic acid-2-phosphate-6-higher fatty acid ester thus obtained with an appropriate base (e.g., sodium hydroxide, potassium hydroxide, magnesium hydroxide, calcium hydroxide, ammonia, monoethanolamine, diethanolamine, triethanolamine, dicyclohexylamine), for example, in a solvent capable of dissolution, such as water or methanol.

Preferred examples of the salt include alkali metals, alkaline earth metals, aluminum, iron, zinc and bismuth. Of these, alkali metals such as sodium and potassium, and alkaline earth metals such as calcium and magnesium are more preferred.

In the compound represented by formula (2), the hydroxyl group at the 3- or 4-position may be protected by a conventionally known group which can be easily transformed to a hydroxyl group, and the present invention includes compounds having such a protective group.

This reaction can be applied not only to the production of the 6-O-higher fatty acid ester of an ascorbic acid-2-phosphate of the present invention, but also to the production of 6-O-lower fatty acid esters thereof.

The ascorbic acid derivative of the present invention exhibits vitamin C activity having both remarkably improved stability and liposolubility as compared with conventionally known ascorbic acid derivatives. Accordingly, vitamin C can be supplied from a preparation having incorporated therein the ascorbic acid derivative of the present invention. Furthermore, when the ascorbic acid derivative of the present invention is blended in a medical preparation, agricultural chemical, food, feed or cosmetic preparation, vitamin C can be effectively supplied.

The ascorbic acid derivatives of the present invention may be used in various medical preparations, for example, as an anti-arhythmic agent, an anti-cerebral infarction agent or an anti-disorder improving agent. These derivatives may be administered orally or parenterally in the form of conventionally used pharmaceutical formulations including, for example, tablets, capsules, liquid preparations or injections. The dosing level depends on the subject to be treated and the manner of administration, but is usually preferably about 0.05 mg/kg to 100 mg/kg body weight, more preferably about 0.5 mg/kg to 25 mg/kg body weight per day for oral administration, and preferably about 1 mg/kg to 10 mg/kg body weight for parenteral administration, and preferably about 0.05 mg/kg to 10 mg/kg body weight per day when administered by injection.

The ascorbic acid derivatives of the present invention are also useful as a cancer metastasis inhibitor and in a pharmaceutical preparation or composition thereof, the ascorbic acid derivative as an active component is generally contained in an amount of from 0.01 to 100% by weight.

Examples of the composition for peroral administration further include a tablet, pill, granule, powder, capsule, syrup, emulsion, suspension and nebula. These compositions can be produced by a known method using a carrier or excipient such as lactose, starch, sucrose or magnesium stearate.

For parenteral administration, for example, an injection, a suppository, a plaster, an ophthalmic solution or a preparation for external application may be used. The injection is usually filled in an appropriate ampule. The suppository includes an endorectal suppository and a vaginal suppository. The preparation for external application includes an ointment, a nasal administration agent and a peroral administration agent.

For formulating a preparation for external application, the composition of the present invention can be formed into a solid, semisolid or liquid solvent thereof according to a known method. For example, in the case of a solid, the composition of the present invention is processed into a powder composition as such or after adding and mixing thereto an excipient (e.g., glycol, mannitol, starch, microcrystal, cellulose) or a thickener (e.g., natural gum, cellulose derivative, acryl polymer).

Similar to the case of an injection, the liquid can be formed as an oily or aqueous suspension. In the case of a semisolid, an aqueous or oily gel or an ointment is preferred.

In any case, a pH adjusting agent (e.g., carbonic acid, phosphoric acid, hydrochloric acid, sodium hydroxide) and an antiseptic (e.g., para-hydroxybenzoic acid esters, chlorobutanol, benzalkonium chloride) may be added. For obtaining a suppository, the composition of the present invention may be formed into an oily or aqueous solid, semisolid or liquid suppository according to a known method.

The ascorbic acid derivatives of the present invention may be blended in various cosmetic preparations as suppliers of vitamin C. Such cosmetic preparations may preferably be used for skin-makeup in the form of a skin-cream, pack or milky lotion. The ascorbic acid derivatives of the present invention may be blended preferably in a range of 0.05 to 5 weight % of the cosmetic preparation. Components which are generally used in cosmetic preparations may be blended in cosmetic preparations together with the ascorbic acid derivatives, so long as the effect of the present invention is obtained. Such components include oils and fats, waxes, hydrocarbons, fatty acids, alcohols, synthetic esters, surface active agents, thickening agents, inorganic chemicals, vitamins, perfumaries and water.

Of the ascorbic acid derivatives of the present invention, the L-form is preferred in view of its vitamin C activity. Particularly, in view of liposolubility, the higher fatty acid ester at the 6-position is preferably a lauric acid ester, a myristic acid ester, a palmitic acid ester or a stearic acid ester.

EXAMPLES

The present invention is described below by reference to the following Examples, however, the present invention should not be construed as being limited thereto.

Example 1

L-Ascorbic acid-2-phosphate-6-palmitate 10 mmol (3.8 g) of magnesium L-ascorbic acid-2-phosphate was dissolved in 60 ml of concentrated sulfuric acid and to the resulting solution, 15 mmol (3.8 g) of palmitic acid was added. The mixed solution thus obtained was homogeneously stirred and after standing at room temperature for 24 hours, the reaction mixture was poured into about 300 ml of ice water. The precipitate was extracted twice with 200 ml of diethyl ether. The extracts were combined and washed with 300 ml of 2N hydrochloric acid containing 30% isopropanol, and the diethyl ether was removed by distillation under reduced pressure. The deposit was washed twice with about 200 ml of n-hexane and then dried under reduced pressure to obtain 3.2 g of L-ascorbic acid-2-phosphate-6-palmitate (yield: 65%). Various analytic data of the compound thus prepared are shown below.

MS m/z=493 [M–H], 495 [M+H], 517 [M+Na]

$^1$H-NMR (400 MHz, CD$_3$OD) δ: 0.90 (3H, t, J=6.9 Hz, 7-H), 1.29 (24H, s, 6-H), 1.63 (2H, hep, J=7.3 Hz, 5-H), 2.38 (2H, t, J=7.4 Hz, 4-H), 4.12–4.30 (3H, m, 2, 3-H), 4.87 (1H, t, J=1.7 Hz, 1-H)

The assignment numbers of the $^1$H-NMR peaks are as follows.

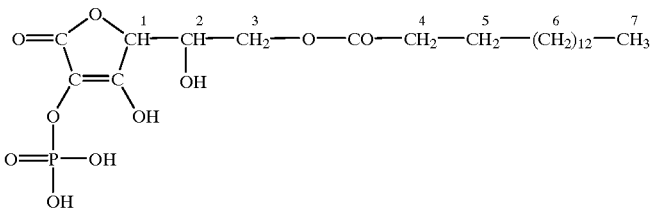

$^{13}$C-NMR (100 MHz, CD$_3$OD) δ: 14.4 (1C, s, 13-C), 23.7 (1C, 12-C), 25.9 (1C, s, 11-C), 30.2–30.7 (10C, s, 10-C), 33.0 (1C, s, 9-C), 34.9 (1C, s, 8-C), 65.5 (1C, s, 7-C), 67.9 (1C, s, 6-C), 77.2 (1C, s, 5-C), 115.3 (1C, d, J=5.7 Hz, 4-C), 160.4 (1C, d, J=3.8 Hz, 3-C), 170.5 (1C, d, J=6.1 Hz, 2-C), 175.1 (1C, s, 1-C)

The assignment number of the $^{13}$C-NMR peaks are as follows.

$^1$H-NMR (400 MHz, CD$_3$OD) δ: 0.90 (3H, t, J=6.8 Hz, 7-H), 1.29 (28H, s, 6-H), 1.61 (2H, hep, J=7.2 Hz, 5-H), 2.37 (2H, t, J=7.3 Hz, 4-H), 4.11–4.31 (3H, m, 2, 3-H), 4.86 (1H, t, J=1.7 Hz, 1-H)

The assignment numbers of the $^1$H-NMR peaks are as follows.

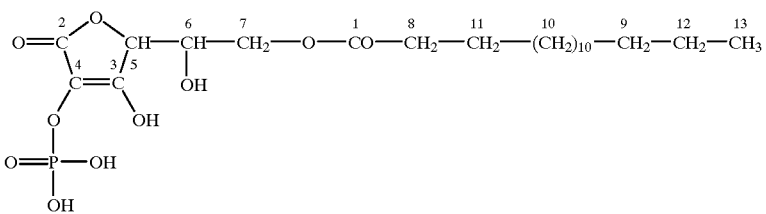

Example 2

L-Ascorbic acid-2-phosphate-6-palmitate

The reaction was performed in the same manner as in Example 1, except for using sodium L-ascorbic acid 2-phosphate in place of magnesium L-ascorbic acid-2-phosphate. As a result, 3.7 g of L-ascorbic acid-2-phosphate-6-palmitate was obtained (yield: 75%).

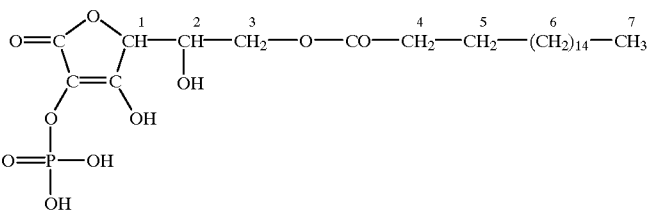

Example 3

L-Ascorbic acid-2-phosphate-6-stearate

The reaction was performed in the same manner as in Example 1, except for using methyl stearate in place of palmitic acid to obtain 4.2 g of L-ascorbic acid-2-phosphate-6-stearate (yield: 81%). Various analytic data of the compound thus obtained are shown below.

MS m/z=521 [M−H], 523 [M+H], 545 [M+Na]

$^{13}$C-NMR (100 MHz, CD$_3$OD) δ: 14.4 (1C, s, 13-C), 23.7 (1C, s, 12-C), 26.0 (1C, s, 11-C), 30.2–30.7 (12C, s, 10-C), 33.0 (1C, s, 9-C), 34.8 (1C, s, 8-C), 65.6 (1C, s, 7-C), 68.0 (1C, s, 6-C), 77.3 (1C, s, 5-C), 115.3 (1C, d, J=6.1 Hz, 4-C), 160.3 (1C, d, J=3.8 Hz, 3-C), 170.5 (1C, d, J=6.1 Hz, 2-C), 175.1 (1C, s, 1-C)

The assignment numbers of the $^{13}$C-NMR peaks are as follows.

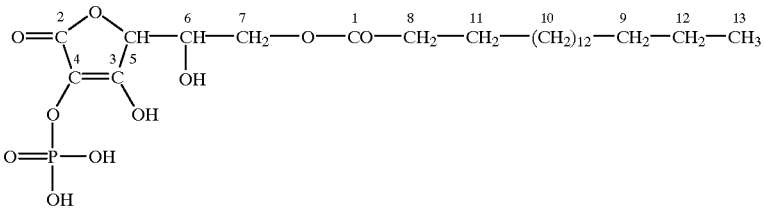

Example 4

L-Ascorbic acid-2-phosphate-6-laurate

The reaction was performed in the same manner as in Example 1, except for using sodium laurate in place of palmitic acid. As a result, 2.2 g of L-ascorbic acid-2-phosphate-6-laurate was obtained (yield: 50%).

Various analytic data of the compound thus prepared are shown below.

MS m/z=439 [M+H], 461 [M+Na], 483 [M+2Na], 505 [M+3Na]

$^1$H-NMR (400 MHz, CD$_3$OD) δ: 0.90 (3H, t, J=6.9 Hz, 7-H), 1.29 (16H, s, 6-H), 1.63 (2H, hep, J=7.3 Hz, 5-H), 2.38 (2H, t, J=7.3 Hz, 4-H), 4.11–4.30 (3H, m, 2, 3-H), 4.86 (1H, t, J=1.7 Hz, 1-H)

The assignment numbers of the $^1$H-NMR peaks are as follows.

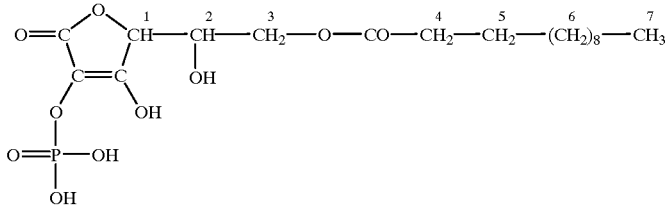

$^{13}$C-NMR (100 MHz, CD$_3$OD) δ: 14.4 (1C, s, 13-C), 23.7 (1C, s, 12-C), 25.9 (1C, s, 11-C), 30.1–30.7 (6C, s, 10-C), 33.0 (1C, s, 9-C), 34.8 (1C, s, 8-C), 65.5 (1C, s, 7-C), 67.9 (1C, s, 6-C), 77.2 (1C, s, 5-C), 115.2 (1C, d, J=5.4 Hz, 4-C), 160.5 (1C, d, J=3.8 Hz, 3-C), 170.5 (1C, d, J=6.1 Hz, 2-C), 175.1 (1C, s, 1-C)

The assignment numbers of the $^{13}$C-NMR peaks are as follows.

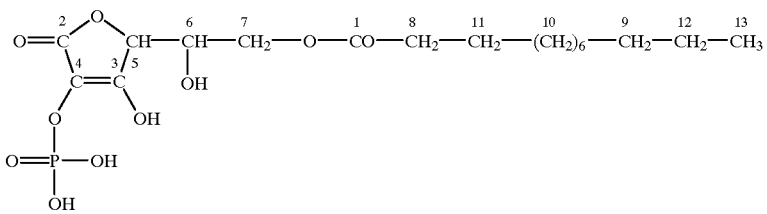

Example 5

L-Ascorbic acid-2-phosphate-6-palmitate magnesium salt

The L-ascorbic acid-2-phosphate-6-palmitate of the present invention was added to purified water to a concentration of 2 mM, and magnesium oxide was gradually added thereto while stirring to effect neutralization (pH: about 8). As a result, L-ascorbic acid-2-phosphate-6-palmitate magnesium salt was obtained.

Example 6

L-Ascorbic acid-2-phosphate-6-palmitate sodium salt

The L-ascorbic acid-2-phosphate-6-palimitate of the present invention was dissolved in methanol to a concentration of 20 mM, and the same volume of a 60 mM sodium hydroxide methanol solution was mixed therewith while stirring. The mixed solution was filtered and the precipitate was collected, washed with a small amount of methanol and dried under reduced pressure to obtain L-ascorbic acid-2-phosphate-6-palmitate sodium salt as a powder product.

Test Example 1

The 2 mM L-ascorbic acid-2-phosphate-6-palmitate magnesium salt obtained in Example 5 and a 2 mM aqueous solution of L-ascorbic acid-2-phosphate magnesium salt having excellent stability were allowed to stand at room temperature for 10 days. Then, their residual ratios (concentration after storage/initial concentration) were determined by HPLC through a column Shodex Asahipak NH2P-50 4E (trade name, manufactured by Showa Denko KK) to evaluate stability. The results are shown in Table 1.

TABLE 1

| Ascorbic Acid (derivative) | Stability (%) |
|---|---|
| L-ascorbic acid-2-phosphate-6-palmitate magnesium salt | 98 |
| L-ascorbic acid-2-phosphate magnesium salt | 97 |

The ascorbic acid derivative of the present invention thus has a stability similar to L-ascorbic acid-2-phosphate magnesium salt.

Test Example 2

About $6 \times 10^5$ cells of a normal human adult mamma epidermal Keratinocyte (available from Kurashiki Boseki KK) were sowed on a 60 mm plate and cultured in a serum-free culturing medium (manufactured by Kurashiki Boseki KK) for 2 hours, and after displacing with the same culturing medium having added thereto from 2 to 50 $\mu$M of an ascorbic acid or a derivative thereof, further cultured for 20 hours. The cells were collected by trypsin treatment, and the number of cells was counted by a Coulter Counter Model DN (trade name, manufactured by Coulter Electronics). The cells thus collected were washed with Hank's equilibrium salt solution, pulverized in an ultrasonic homogenizer, filtered through a Mol-cut II (UFPlLCC) (trade name, produced by Nippon Milipore KK) and analyzed by HPLC through a column Shodex Asahipak NH2P-50 4E (trade name, produced by Showa Denko KK). The amount of ascorbic acid and derivatives thereof was measured to determine the intracellular cumulative amount. As a control, culturing was performed in the same manner as above except for not adding ascorbic acid or a derivative thereof, and the ascorbic acid was quantitatively determined. The difference in the intracellular ascorbic acid cumulative amount between the case where ascorbic acid or a derivative thereof was added and the case where ascorbic acid or a derivative thereof was not added is shown in Table 2.

The L-ascorbic acid-2-phosphate-6-fatty acid esters or salts thereof thus used were prepared by or in accordance with the methods described in the respective Examples. The 6-O-pivaloyl-L-ascorbic acid-3-phosphate was prepared by the method described in JP-B-3-55470. The 2-O-D-glucopyranosil-L-ascorbic acid was extracted from UV White (trade name, produced by Shiseido Co., Ltd.). Other reagents used herein were commercially available products.

TABLE 2

| Ascorbic Acid (Derivative) and Addition Amount | | Intracellular Cumulative Amount Pmole/cell |
|---|---|---|
| L-Ascorbic acid 2-phosphate-6-palmitate | 2 $\mu$M | 0.0042 |
| L-Ascorbic acid 2-phosphate-6-palmitate sodium salt | 2 $\mu$M | 0.0040 |
| L-Ascorbic acid 2-phosphate-6-laurate | 2 $\mu$M | 0.0042 |
| L-Ascorbic acid 2-phosphate-6-laurate magnesium salt | 2 $\mu$M | 0.0033 |
| L-Ascorbic acid 2-phosphate-6-stearate | 2 $\mu$M | 0.0034 |
| L-Ascorbic acid | 2 $\mu$M | <0.0002 |
| L-Ascorbic acid | 50 $\mu$M | 0.0003 |
| L-Ascorbic acid-2-phosphate sodium salt | 2 $\mu$M | <0.0002 |
| L-Ascorbic acid-2-phosphate magnesium salt | 2 $\mu$M | <0.0002 |
| L-Ascorbic acid-2-phosphate magnesium salt | 50 $\mu$M | 0.0022 |
| 6-O-Pivaloyl-L-ascorbic acid-3-phosphate | 2 $\mu$M | 0.0005 |
| L-Ascorbic acid-2-phosphate sodium salt | 2 $\mu$M | <0.0003 |
| 2-O-D-Glucopyranosil-L-ascorbic acid | 2 $\mu$M | <0.0002 |
| L-Ascorbic acid-6-palmitate | 2 $\mu$M | 0.0009 |
| L-Ascorbic acid-2,6-dipalmitate | 2 $\mu$M | <0.0002 |
| Not added | | 0.0000 |

The derivatives of the present invention can yield an ascorbic acid intracellular cumulative amount equal to or greater than that attained when ascorbic acid or a conventional ascorbic acid derivative (for example, ascorbic acid-2-phosphate magnesium salt) is used, with a very low concentration (1/10 or less as compared with conventional derivatives). These results show that the effect of vitamin C can be very easily obtained using the ascorbic acid derivative of the present invention.

Example 7

Feed Composition Product 30 g of L-ascorbic acid-2-phosphate-6-palmitate sodium salt of the present invention and 15 g of "Lucarotene 10%" (produced by BASF, β-carotene content: 10%) and wheat flour were mixed to make a total amount of 300 g. The mixture thus obtained was fed together with 30 ml of water to an extruder, kneaded, extruded into a stick, cut and dried to produce vitamin C enriched pellets for livestock, poultry and marine animals, each having a diameter of 3.2 mm and a length of 5 mm.

Example 8

Skin Cream

| | |
|---|---|
| squalene | 5.0 wt % |
| cetyl alcohol | 1.5 |
| polyoxyethylene (20) sorbitan monostearate | 2.0 |
| polyoxyethylene (20) cetyl ether | 1.5 |
| vaseline | 6.0 |
| 1,3-buylene glycol | 7.5 |
| L-Ascorbic acid 2-phosphate-6-palmitate | 4.5 |
| sodium citrate | 0.5 |
| methyl p-hydroxybenzoate | 0.2 |
| perfumary | 0.01 |
| purified water | remainder |

This mixture was stirred at 80° C. and then cooled to produce a skin-cream.

Example 9

Milky Lotion

| | |
|---|---|
| squalene | 3.0 wt % |
| vaseline | 2.0 |
| microcrystaline wax | 1.0 |
| stearyl alcohol | 0.5 |
| dl-α-tocopherol | 1.0 |
| sorbitan fatty acid ester | 1.5 |
| polyoxyethylene (20) sorbitan monooleic acid ester | 2.0 |
| glycerol | 5.0 |
| L-Ascorbic acid 2-phosphate-6-laurate | 1.5 |
| perfumary | 0.01 |
| purified water | remainder |

This mixture was stirred at 70° C. and then cooled to produce a milky lotion.

The novel ascorbic acid derivative of the present invention has facilitated cellular uptake, and can increase the ascorbic acid intracellular cumulative concentration with a small dose. By using the ascorbic acid derivative of the present invention, vitamin C can be effectively supplied and its action can be easily brought about.

While the invention has been described in detail and with reference to specific embodiments thereof, it will be apparent to one skilled in the art that various changes and modifications can be made therein without departing from the spirit and scope thereof.

What is claimed is:

1. A process for producing an ascorbic acid derivative which is a compound represented by the following formula (1) or a salt thereof, which comprises reacting an ascorbic acid-2-phosphoric-acid ester or 2-pyrophosphoric acid ester or 2-triphosphoric acid ester and/or a salt thereof with at least one of a fatty acid, a fatty acid ester thereof and a salt thereof to produce a compound represented by formula (1) of a salt thereof:

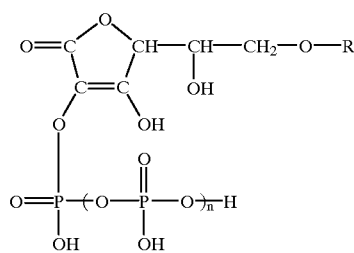

(1)

wherein R represents an acyl group having eleven or more carbon atoms and n is 0, 1 or 2, and said reacting step comprises reacting in the presence of an acidic condensing agent.

2. A process for producing an ascorbic acid derivative which is a compound represented by the following formula (2) or a salt thereof, which comprises reacting an ascorbic acid-2-phosphoric acid ester and/or a salt thereof with at least one of a fatty acid, an ester thereof and a salt thereof to produce a compound represented by formula (2) or a salt thereof:

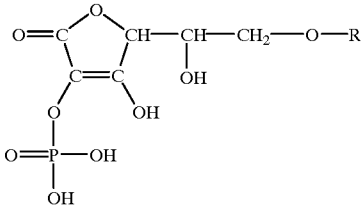

(2)

wherein R represents an acyl group having eleven or more carbon atoms, and said reacting step comprises reacting in the presence of an acidic condensing agent.

3. The process for producing an ascorbic acid derivative as claimed in claim 1, wherein said reacting step comprises reacting in concentrated sulfuric acid.

4. The process for producing an ascorbic acid derivative as claimed in claim 2, wherein said reacting step comprises reacting in concentrated sulfuric acid.

5. An agricultural chemical preparation, medical preparation, animal drug preparation, food or feed composition containing an ascorbic acid derivative which is a compound represented by the following formula (1) of a salt thereof:

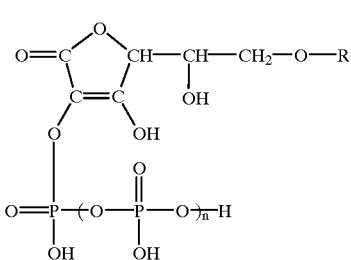

(1)

wherein R represents an acyl group having eleven or more carbon atoms and n is 0, 1 or 2.

6. The agricultural chemical preparation, medical preparation, animal drug preparation, food or feed composition as claimed in claim 5, wherein R in formula (1) is selected from the group consisting of a lauroyl group, a myristoyl group, a palmitoyl group and a stearoyl group.

7. The agricultural chemical preparation, medical preparation, animal drug preparation, food or feed composition as claimed in claim 5, wherein the salt is a salt of a metal selected from the group consisting of alkali metals, alkaline earth metals, aluminum, iron, zinc and bismuth.

* * * * *